United States Patent [19]

Baldwin et al.

[11] 4,346,042
[45] Aug. 24, 1982

[54] PREPARATION OF EPIHALOHYDRIN ENANTIOMERS

[75] Inventors: John J. Baldwin, Lansdale; David E. McClure, Hatfield, both of Pa.

[73] Assignee: Merck & Co., Inc., Rahway, N.J.

[21] Appl. No.: 146,927

[22] Filed: May 5, 1980

Related U.S. Application Data

[60] Division of Ser. No. 940,681, Sep. 8, 1978, abandoned, which is a continuation-in-part of Ser. No. 919,590, Jun. 27, 1978, abandoned.

[51] Int. Cl.³ .......................................... C07D 303/34
[52] U.S. Cl. .................................. 549/557; 544/134; 549/430
[58] Field of Search .................................. 260/348.43

[56] References Cited

U.S. PATENT DOCUMENTS 2,755,290  7/1956  Mueller ......................... 260/348.43
3,290,336  12/1966  McClure ....................... 260/348.57

Primary Examiner—Ethel G. Love
Attorney, Agent, or Firm—Daniel T. Szura; Harry E. Westlake, Jr.

[57] ABSTRACT

Processes for preparing (S) or (R) epihalohydrin and an (S) substituted glycerol intermediate are disclosed.

2 Claims, No Drawings

PREPARATION OF EPIHALOHYDRIN ENANTIOMERS

This is a division of application Ser. No. 940,681, filed Sept. 8, 1978, now abandoned, which in turn is a continuation-in-part of U.S. Ser. No. 919,590, filed June 27, 1978, now abandoned.

BACKGROUND OF THE INVENTION

The present invention is concerned with processes for preparing epihalohydrin enantiomers and intermediates.

Epibromohydrin enantiomers have been prepared by a resolution process—and an epichlorohydrin enantiomer has been prepared from 1-bromo-3-chlorpropan-2-ol. enantiomer derived from the epibromohydrin [Chemische Berichte 48, 1862-184, (1915)].

An improved method for preparing the epihalohydrin enantiomers from sulfonyloxyhaloalcohol has been discovered—and an improved process for preparing an intermediate useful in the synthesis has also been discovered.

SUMMARY OF THE INVENTION

Process for (a) preparing (S) or (R) epihalohydrin from an (S) or (R) sulfonyloxyhaloalcohol and (b) preparing (S) glycerol-1, 2-acetonide from isopropylidine-D-mannitol.

DESCRIPTION OF THE PREFERRED EMBODIMENTS

An embodiment of the present invention is a process for preparing an enantiomer of epihalohydrin which comprises treating an enantiomer of an alcohol having the formula $$Z-SO_2-O-CH_2-\overset{OH}{\underset{|}{CH}}-CH_2-X \quad (I)$$

wherein Z is phenyl, monosubstituted phenyl, CF$_3$ or C$_1$-C$_6$ alkyl and X is Cl or Br with an alkali metal glycolate and recovering said epihalohydrin by distillation.

The reaction is illustrated by the following equation:

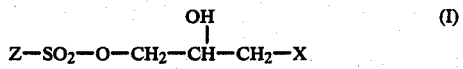

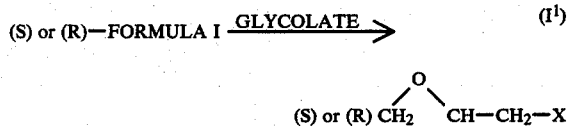

The product is recovered in good yield by direct vacuum distillation at room temperature from the reaction mixture.

Z may be phenyl, monosubstituted phenyl or C$_1$-C$_6$ alkyl. The monosubstituted phenyl group is exemplified by C$_1$-C$_3$-alkylphenyl e.g. p-propylphenyl, o-methylphenyl, and m-ethylphenyl, p-NO$_2$-phenyl, p-OCH$_3$-phenyl, 2-chlorophenyl and the like. The C$_1$-C$_6$ alkyl group includes CH$_3$, C(CH$_3$)$_3$, isopropyl, n-hexyl and the like. The p-methylphenyl and CH$_3$ groups are preferred.

The alkali metal glycolate includes K or Na ethylene glycolate, with Na ethylene glycolate being preferred.

When a more conventional low boiling solvent/strong base, e.g. methanol/NaOCH$_3$ is used in place of the glycolate in reaction (I$^1$), the product yield obtained on direct vacuum distillation at room temperature is low.

Another embodiment of the present invention is a process for preparing (S)-glycerol-1, 2-acetonide of the formula

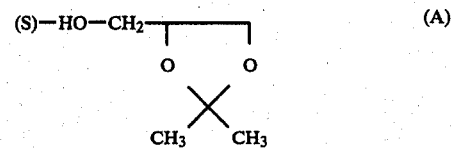

which comprises a (a) treating 1,2:5,6-di-O-isopropylidine-D-mannitol having the formula

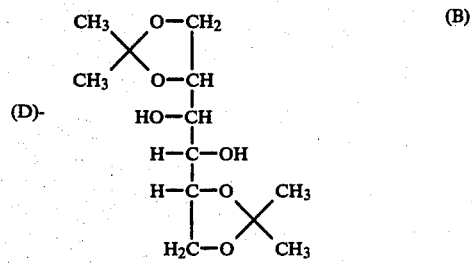

with lead tetraacetate in a suitable solvent and (b) reducing the reaction product from (a) with alkalimetal borohydride and (c) treating the reaction mixture from (b) with an ammonium halide.

Suitable solvents include aprotic compounds such as tetrahydrofuron (THF), ethylacetate, dimethylformamide (DMF) and the like. THF and ethylacetate are preferred solvents.

Ammonium halides include NH$_4$Br and NH$_4$Cl. NH$_4$Cl is preferred.

The reaction of (B) with Pb(OAc)$_4$ in step (a) may be carried out at any convenient temperature. Temperatures below about 10° C. are preferred. The preferred molar nature of leadtetraacetate to (B) is about 1:1.

The reduction of the step (b) is also carried out at a convenient temperature. Preferred temperatures are below about 10° C. The NaBH$_4$ reducing agent is generally added to the reaction mixture in solution e.g. in aqueous NaOH. The amount of NaBH$_4$ may be varied. It is preferred that about 2 moles of NaBH$_4$ per mole of (B) reactant be used.

The reaction of step (b) is allowed to proceed for a period sufficient for the reaction to be complete, e.g. for about 30 minutes at about 0° C. and for about 90 minutes at room temperature. At the appropriate time, NH$_4$Cl is added to solution until the PH reaches about 8. After the reaction solvent is removed under reduced pressure, the produce (A) is recovered using conventional procedures.

When sodium periodate [Synthesis 423 (1977); Biochemistry 3, 976 (1964)] is used in place of Pb(OAc)$_4$ the product obtained is generally racemic.

When H$_2$/Raney nickel [J. Biol. hem. 128, 463 (1939)] is used in place of the NaBH$_4$, yields obtained are variable depending on the quality of the Raney nickel.

The formula (A) glycerol is especially useful as an intermediate in the preparation of (S) and (R) epihalohydrins. The following flow sheet illustrates this utility:

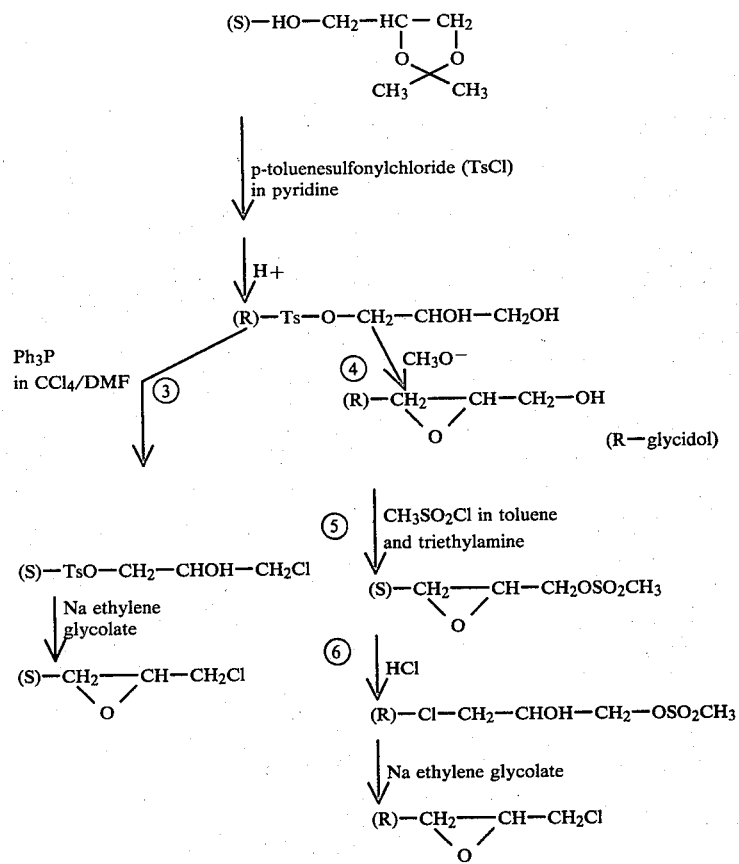

Reactions related to 1 and 2 are disclosed in J.A.C.S. 64, 1291 (1942). Reaction 3 is related to that described in Tetrahedron Letters, 4361 (1969). Reaction sequence 5 and 6 has been carried out with racemic reactants [Bull. Chem. Soc. Japan 39, 413 (1966)].

The preparation illustrated by the flow sheet shows that either the (S) or (R) enantiomer of an epihalohydrin, especially epichlorohydrin, can be prepared directly from a common starting material [compound (A) or product (B)] without requiring costly and inefficient resolution procedures. This constitutes another aspect of the present invention.

Epihalohydrins have wide utility in organic synthesis. The enantiomers of epihalohydrin may be especially useful to prepare intermediates which in turn can be used to prepare specific isomers which have pharmaceutical utility. One such preparation is illustrated by the following reaction equations:

REACTION SEQUENCE A

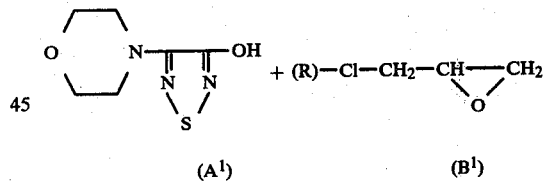

STEP 1

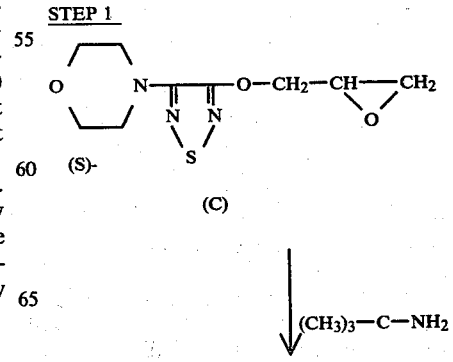

STEP 2

-continued

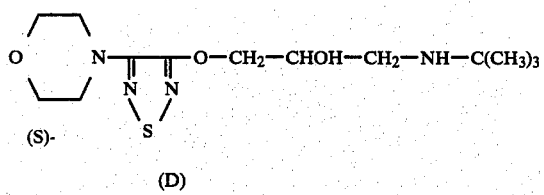

(D)

The product (C) is a commercial β-adrenergic blocking agent.

Other preparations utilizing the Step 1, sequence A type reaction are illustrated by the following reaction equation:

REACTION B

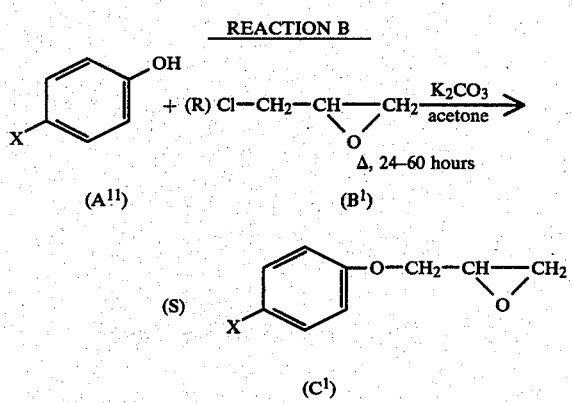

X in this equation is H, CHO, CN or OCH₃.

Where a stronger base, such as NaH in DMF, is used in the above reactions, the intermediate (C or C¹) is obtained as a mixture of (S) and (R) isomer.

Another aspect of the present invention relates to the novel sulfonyl intermediates of the type obtained in Step (5) in the above flow sheet. These compounds are represented by the formula

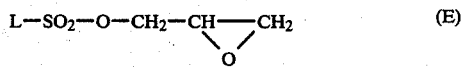

where L may be an alkyl group such as $CH_3$, $C_4H_9$, $CF_3$— and the like, or a phenyl group such as phenyl, p-chlorophenyl, p-tolyl, p-nitrophenyl and the like.

The formula (E) compounds are useful as intermediates in reactions related to Reactions A and B as illustrated by the following equation:

REACTION C

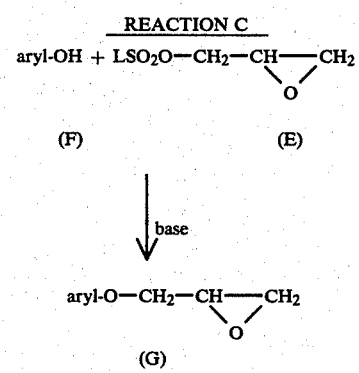

aryl includes groups such as phenyl,

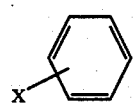

where X is a substituent such as chloro, CHO, CN, $C_1$-$C_4$ alkoxy and the like, pyridyl, cyanopyridyl 4-morpholino-1,2,5-thiadiazolyl and the like.

When an enantiomer i.e. (R) or S isomer, of the (E) compound is used in the reaction, the type of base and the L group have an effect on the isomer configuration of the final product. Illustrating this effect are the following two equations:

REACTION D

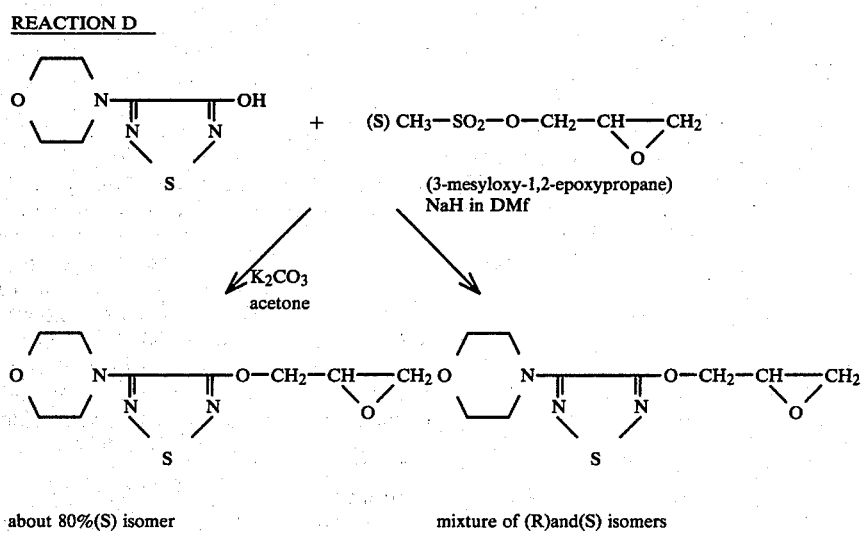

REACTION E

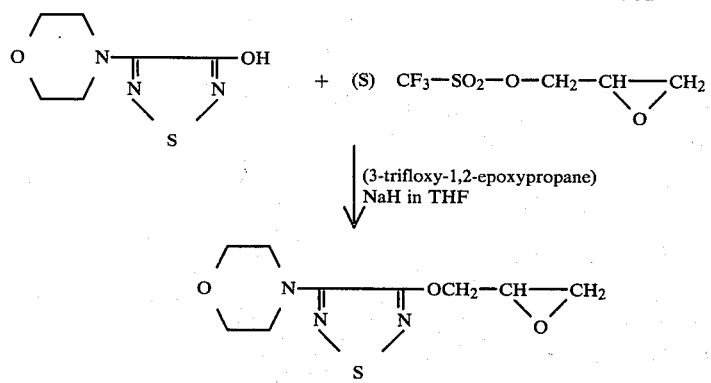

100% (S) isomer

Thus, where L is CF$_3$ and a strong base is used, the (S) isomer of the formula (E) compounds yields the (S) isomer of the formula (G) compound. Therefore, by utilizing an enantiomer of 3-trifloxy-1,2-epoxypropane and a suitable base in the (C) reaction the isomeric configuration of the trifloxy enantiomer is maintained in the product. If an enantiomer of mesyloxy mesyloxyepoxypropane is used, a mixture of enantiomers is obtained.

The following example describes the preparation of (S)-3-trifloxy-1,2-epoxypropane. All temperatures are in °C.

EXAMPLE A

To pyridine (10.3 g, 0.13 m) in CH$_2$Cl$_2$ (300 ml) cooled to −23° in a dry ice/CCl$_4$ bath was added trifluoromethanesulfonic anhydride (36.7 g, 0.13 m) in CH$_2$Cl$_2$ (100 ml) dropwise over ½ hour. While still cooling this mixture at −23°, (R)-glycidol (8.6 g, 0.116 m) in CH$_2$Cl$_2$ (100 ml) was added dropwise over ½ hour. After stirring for 5 minutes with cooling and 15 minutes without, an equal volume of hexane was added and the solids were filtered. Concentration of the solution at 30°/25 torr. left a residue which was distilled to give (S)-3-trifloxy-1,2-epoxypropane (40%); b.p. 35°–39°/0.2 mm; $[\alpha]_D^{24} = 14.7°$ (c=3.90, CHCl$_3$); 1H NMR (CDCl$_3$) 4.8 (1H, d of d, J=11, J=3), 4.4 (1H, d of d, J=11, J=3), 3.3 (1H, m), 2.9 (1H, t, J=4.5), 2.7 (1H, J=4.5, J=2).

The following examples illustrate the processes of the present invention. All temperatures are in °C.

EXAMPLE 1

(S)-Glycerol-1,2-acetonide

To an ice-cooled solution of 1,2:5,6-di-O-isopropylidine-D-mannitol (80.0 g., 0.3 ml) in THF (400 m) was added portionwise with stirring dry Pb(OAc)$_4$ (134 g, 0.3 m), while maintaining the temperature below 10° C. The solution was stirred for 30 minutes with ice cooling and an additional 30 minutes without. After filtering through Super-Cel and cooling in an ice bath, a solution of NaBH$_4$ (22.9 g, 0.62 m) in 4% aqueous NaOH (400 ml) was added dropwise with vigorous stirring while maintaining the temperature below 10° C. After stirring in an ice bath for 30 minutes and at room temperature for 90 minutes, solid ammonium chloride was added to the solution until it buffered at about pH 8. The THF was removed under reduced pressure, and the resulting aqueous solution was saturated with NaCl. After extracting into ethyl acetate, the organic layer was washed with 5% aqueous NaOH saturated with NaCl, dried (Na$_2$SO$_4$), and concentrated. Distillation afforded pure (S)-glycerol-1,2-acetonide (58.4 g, 73%); bp 80°–90° C./20 mm; 1H NMR (CDCl$_3$) 1.45 (6H, s), 3.5–4.5 (6H, m); $[\alpha]_D^{25} = 11.3°$ (c=5.174, CH$_3$OH).

EXAMPLE 2

(a) (R)-3-Tosyloxy-1,2-propanediol

To an ice-cooled solution of (S)-glycerol-1,2-acetonide (72.0 g, 0.55 m) in pyridine (300 ml) was added portionwise with stirring p-toluenesulfonyl chloride (104.0 g, 0.55 m). After standing in a refrigerator for 16 hours, the reaction mixture was diluted with ether (300 ml), washed with 1 NHCl until the aqueous wash was acidic, and then washed with saturated aqueous NaHCO$_3$. The ether layer was dried (Na$_2$SO$_4$) and concentrated to give (R)-3-toxyloxypropanediol acetonide (141.0 g, 91%), which was used without further purification.

The acetonide from above in acetone (100 ml) and 1 NHCl (300 ml) was heated on a steam bath for 30 minutes. The resulting solution was concentrated to dryness, and the residue was dissolved in CH$_2$Cl$_2$. After drying (Na$_2$SO$_4$) and concentration, the resulting oil solidified upon standing. Residual solvents were removed at 25° C. and 0.5 mm over 18 hours to give (R)-3-tosyloxy-1,2-propanediol, (121.0 g, 100%); mp 54°–59° C. (lit=61°–63° C.); 1H NMR (CDCl$_3$) 2.4 (3H, s), 3.3–4.3 (7H, m), 7.35 and 7.8 (4H, 2d, J=8).

(b) (R)-Glycidol

To an ice-cooled solution of (R)-3-tosyloxy-1,2-propanediol (120.5 g, 0.49 m) in methanol (200 ml) and ether (100 ml) was added sodium pellets (10.7 g, 0.45 m) in three portions over approximately 1 hour. Stirring was continued with ice cooling for 1 hour. The reaction mixture was concentrated at 30° C., and the residue was taken up in ether. After filtration, the solvent was removed at 30° C./25 mm, and the residue was treated with chloroform and reconcentrated to remove the last traces of methanol. An additional chloroform treatment as above gave (R)-glycidol (33.5 g, 93%), which was used without purification in subsequent steps.

(c) (S)-3-Mesyloxy-1,2-epoxypropane

To an ice-cooled solution of (R)-glycidol (5.0 g, 0.068 m) and triethylamine (8.1 g, 0.080 m) in toluene (100 ml)

was added, over 15 minutes, methanesulfonyl chloride (8.0 g, 0.070 m) in toluene (25 ml). Stirring was continued with cooling for 1 hour. The solution was filtered and concentrated to give an 80–85% yield of the crude (S)-3-mesyloxy-1,2-epoxypropane; this material could be used without further purification. Distillation gave 7 (61%); bp 92°–95° C./0.1 mm; $[\alpha]_D^{22} = 23.7°$ (c=5.16, CH$_3$OH); $^1$H NMR (CDCl$_3$) 4.5 (1H, d of d, J=12, J=3), 4.1 (1H, d of d, J=12, J=6), 3.3 (1H, m), 3.1 (3H, s), 2.8 (2H, m).

(d) (R)-Epichlorohydrin

Concentrated HCl (20 ml) was added to (S)-3-mesyloxy-1,2-epoxypropane (5.0 g, 0.033 m) over 15–20 minutes. After stirring for an additional 30 minutes, the water was removed through the addition and subsequent evaporation of ethanol. Finally, residual ethanol was removed at room temperature and 0.1 mm to give (R)-3-mesyloxy-2-hydroxy-1-chloropropane, (5.4 g, 85%); $^1$H NMR (CDCl$_3$) 4.35 (2H, d), 4.1 (1H, m), 3.65 (2H, d), 3.1 (3H, s), 2.9 (1H, broad s); $[\alpha]_D^{22} = 7.1°$ (c=5.78, CH$_3$OH).

To (R)-3-mesyloxy-2-hydroxy-1-chloropropane (5.4 g, 0.029 m) in dry ethylene glycol (20 ml). After stirring for 15 minutes, (R)-epichlorohydrin (2.2 g, 86%) was distilled from the reaction mixture at room temperature and 0.2 mm and trapped in dry ice/acetone; $^1$H NMR (CDCl$_3$) & 3.6 (2H, d), 3.2 (1H, m), 2.8 (2H, m); $[\alpha]_D^{22} = 33.0°$ (c=4.22, CH$_3$OH).

A small sample was further purified by preparative GC on an HP 5710 A instrument using a 6′ 5% OV-17 column with an oven temperature of 60° C. to give (R)-epichlorohydrin; $[\alpha]_D^{23} = 34.3°$ (c=1.50, CH$_3$OH).

EXAMPLE 3
(S)-Epichlorohydrin

To triphenylphosphine (13.2 g, 0.05 m) in CCl$_4$ (20 ml) and DMF (50 ml), (R)-3-tosyloxy-1,2-propanediol (12.3 g, 0.05 m) in DMF (50 ml) was added all at once. After the addition was complete, the temperature increased to 50° C. over 15 minutes. The mixture was then allowed to stir for 3 hours. The residual solvents were removed (50° C., 2 mm) and the residue was taken up in H$_2$O, dried (Na$_2$SO$_4$), and concentrated. Residual solvents were removed at 25° C. and 0.2 mm over 18 hours.

To this residue, composed of triphenylphosphine oxide and (S)-3-tosyloxy-2-hydroxy-1-chloropropane, in dry ethylene glycol (50 ml) was added a solution of sodium ethylene glycolate [from sodium pellets (1.25 g, 0.054 m)] in dry ethylene glycol (50 ml). After stirring for 15 minutes, (S)-epichlorohydrin was distilled from the reaction mixture at room temperature and 0.2 mm and trapped in dry ice/acetone. The $^1$H NMR indicated that traces of CH$_2$Cl$_2$ and H$_2$O were present; $[\alpha]_D^{20} = 28.1°$ (c=2.47, CH$_3$OH).

A small sample was purified by preparative GC to yield pure (S)-epichlorohydrin $[\alpha]_D^{23} = 33.0°$ (c=2.47, CH$_3$OH).

Analogous epibromohydrins are obtained when the corresponding bromo reactants replace the chloro reactants in Examples 2 and 3.

Claims to the invention follow.

What is claimed is:

1. An (R) or (S) isomer of a compound of the formula

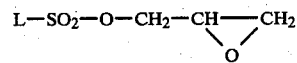

wherein L is CF$_3$.

2. The (S) isomer of the claim 1 compound.

* * * * *